US012779189B2

(12) United States Patent
Akerele et al.

(10) Patent No.: US 12,779,189 B2
(45) Date of Patent: Nov. 3, 2026

(54) WRINKLE DETECTION AND TREATMENT SYSTEM

(71) Applicant: L'Oreal, Paris (FR)

(72) Inventors: Dominic Akerele, Brooklyn, NY (US); Richard Besen, New York, NY (US); Fred Orsita, New York, NY (US); Guive Balooch, Paris (FR)

(73) Assignee: L'Oréal, Paris (FR)

( * ) Notice: Subject to any disclaimer, the term of this patent is extended or adjusted under 35 U.S.C. 154(b) by 0 days.

(21) Appl. No.: 18/060,220

(22) Filed: Nov. 30, 2022

(65) Prior Publication Data

US 2023/0241364 A1 Aug. 3, 2023

Related U.S. Application Data

(60) Provisional application No. 63/304,466, filed on Jan. 28, 2022.

(30) Foreign Application Priority Data

Mar. 3, 2022 (FR) ...................................... 2201839

(51) Int. Cl.
*A61M 35/00* (2006.01)
*A61B 5/00* (2006.01)

(52) U.S. Cl.
CPC ......... *A61M 35/003* (2013.01); *A61B 5/0077* (2013.01); *A61B 5/442* (2013.01); *A61M 2205/3303* (2013.01)

(58) Field of Classification Search
CPC ........ A61M 35/003; A61M 2205/3303; A61B 5/0077; A61B 5/442; A61B 5/0064; A61B 5/0059; G06V 10/56; G06V 40/162; G06V 2201/03; G06T 7/11; G06T 7/143; G06T 7/136; G06T 2207/30088
See application file for complete search history.

(56) References Cited

U.S. PATENT DOCUMENTS 10,004,885 B2 6/2018 Casasanta, III et al.
10,071,233 B2 9/2018 Casasanta, III et al.
10,076,646 B2 9/2018 Casasanta, III et al.
10,188,192 B2 1/2019 Rabe et al.
11,090,474 B2 * 8/2021 Edgar ....................... G06T 7/11
2006/0098076 A1 * 5/2006 Liang .................. A45D 44/005 347/129
2008/0294012 A1 * 11/2008 Kurtz ..................... A61B 5/444 600/300
2011/0155161 A1 * 6/2011 Samain ................ A45D 44/005 401/137

(Continued)

*Primary Examiner* — Rebecca E Eisenberg
*Assistant Examiner* — Timothy L Flynn
(74) *Attorney, Agent, or Firm* — CHRISTENSEN O'CONNOR JOHNSON KINDNESS PLLC

(57) ABSTRACT

A system for treating skin, the system including at least one cartridge containing a skincare material, a dispensing device comprising at least one chamber configured to accept the at least one cartridge, and a processor communicatively coupled to the dispensing device, wherein the processor is configured to visualize an image of a user's skin, detect one or more features on the user's skin with image processing, and apply the skincare product onto the one or more skin conditions to the user's skin through an applicator on the dispensing device.

17 Claims, 6 Drawing Sheets

(56) References Cited

U.S. PATENT DOCUMENTS

| | | | | |
|---|---|---|---|---|
| 2012/0017929 | A1* | 1/2012 | Samain | A61K 8/4986 132/288 |
| 2015/0057623 | A1* | 2/2015 | Hyde | A61B 5/441 604/289 |
| 2015/0379369 | A1* | 12/2015 | Liang | G06T 11/00 348/77 |
| 2016/0058156 | A1* | 3/2016 | Chiasson | A45D 40/261 132/200 |
| 2018/0014777 | A1* | 1/2018 | Amir | A61M 35/003 |
| 2018/0369077 | A1 | 12/2018 | Giron et al. | |
| 2018/0369078 | A1 | 12/2018 | Giron et al. | |
| 2020/0098174 | A1* | 3/2020 | Charraud | G06V 20/64 |
| 2020/0196734 | A1* | 6/2020 | Meschkat | A61B 5/442 |
| 2021/0046296 | A1* | 2/2021 | Binner | A61M 35/003 |
| 2022/0051409 | A1* | 2/2022 | Maclellan | A61B 5/1032 |

* cited by examiner

WRINKLE DETECTION AND TREATMENT SYSTEM

CROSS-REFERENCES TO RELATED APPLICATIONS

The present application claims priority to and the benefit of U.S. Provisional Application No. 63/304,466, filed Jan. 28, 2022, and French Application No. 2201839, filed Mar. 3, 2022, the entire disclosures of which are hereby incorporated by reference herein in their entirety for all purposes.

SUMMARY

This summary is provided to introduce a selection of concepts in a simplified form that are further described herein in the Detailed Description. This summary is not intended to identify key features of the claimed subject matter, nor is it intended to be used as an aid in determining the scope of the claimed subject matter.

As we age, we develop wrinkles, fine lines, and other skin conditions. In some cases, it can be difficult to detect where these wrinkles begin and end, and treatment often includes invasive techniques, including the use of needles. Described herein is a system of detecting skin features such as wrinkles, fine lines, and pigmentation, and an applicator capable of treating and concealing the skin features in a precise and localized manner, without the use of invasive methods. Also described herein is a system for applying localized makeup to the face, such as by coloring a user's eyebrows, or applying eyeliner.

In one aspect, a system for treating skin, the system comprising at least one cartridge containing a skin formula, a dispensing device comprising configured to accept the at least one cartridge, and a processor communicatively coupled to the dispensing device, wherein the processor is configured to visualize an image of a user's skin, detect one or more features on the user's skin with image processing, and apply the skin formula onto the one or more skin conditions to the user's skin through an applicator on the dispensing device is disclosed.

In another aspect, a method of applying a skin treatment with the system of any of the preceding claims, the method comprising visualizing an image of a user's skin, detecting one or more features on the user's skin with image processing, and applying the skin formula onto the one or more features on the user's skin through the applicator on the dispensing device is disclosed.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

While illustrative embodiments have been illustrated and described, it will be appreciated that various changes can be made therein without departing from the spirit and scope of the invention.

Described herein are systems and methods for detecting a feature on a user's skin and applying a skin formula precisely to the feature. In some embodiments, the feature is a wrinkle, a fine line, pigmentation, hyperpigmentation, or acne. In some embodiments, the feature is an eyebrow, an upper lash line, a lower lash line, or a waterline. In some embodiments, the skin formula is a skin treatment such as a wrinkle or acne treatment. In some embodiments, the treatment is a concealer. In some embodiments, the skin formula is a skin treatment and a concealer. In some embodiments, the skin treatment is a cosmetic such as a brow tint or an eyeliner. In some embodiments, the skincare device includes an IR camera and an optical sensor to visualize images of the user's skin as they move the device over their face. In some embodiments, a processor on the skincare device detects the skin feature using image processing. In some embodiments, the image processing includes segment-based image processing. In some embodiments, the image processing includes a facial landmark detection algorithm. In an embodiment, the user actuates a user input to direct the skincare device to apply the skin formula.

In an embodiment, the skincare device is communicatively coupled to a communication device, such as a smartphone. In some embodiments, the user can direct the skincare device to begin taking images or apply the skin formula through an interface on the communication device. In some embodiments, the skincare device or the communication device can alert the user that the skin formula will be applied.

In some embodiments, a system for treating skin, the system comprising at least one cartridge containing a skin formula, a dispensing device configured to accept the at least one cartridge, and a processor communicatively coupled to the dispensing device, wherein the processor is configured to visualize an image of a user's skin, detect one or more features on the user's skin with image processing, and apply the skin formula onto the one or more skin conditions to the user's skin through an applicator on the dispensing device is disclosed.

In some embodiments, the skincare device is configured to accept one or more cartridges containing a skin formula. In some embodiments, the skin formula is a skin treatment, such as a wrinkle treatment or an acne treatment. In some embodiments, the skin formula is a cosmetic, such as a concealer, a brow tint, or an eyeliner. In some embodiments, the skin formula is both a skin treatment and a concealer.

Figure 1A:
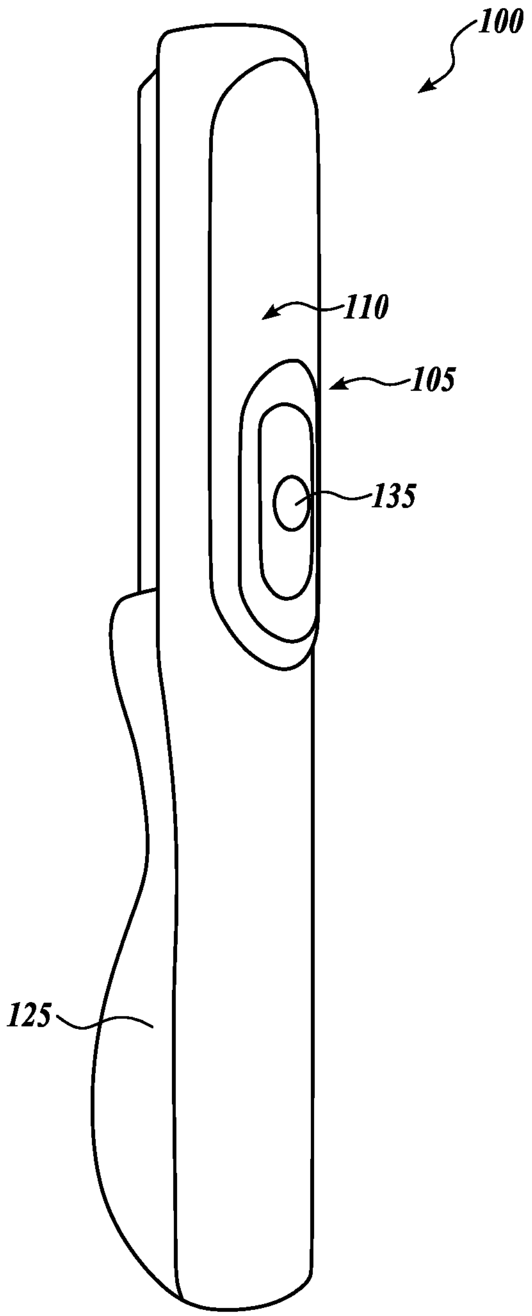
FIGS. 1A-1B are example skincare devices, in accordance with the present technology.
Figure 1B:
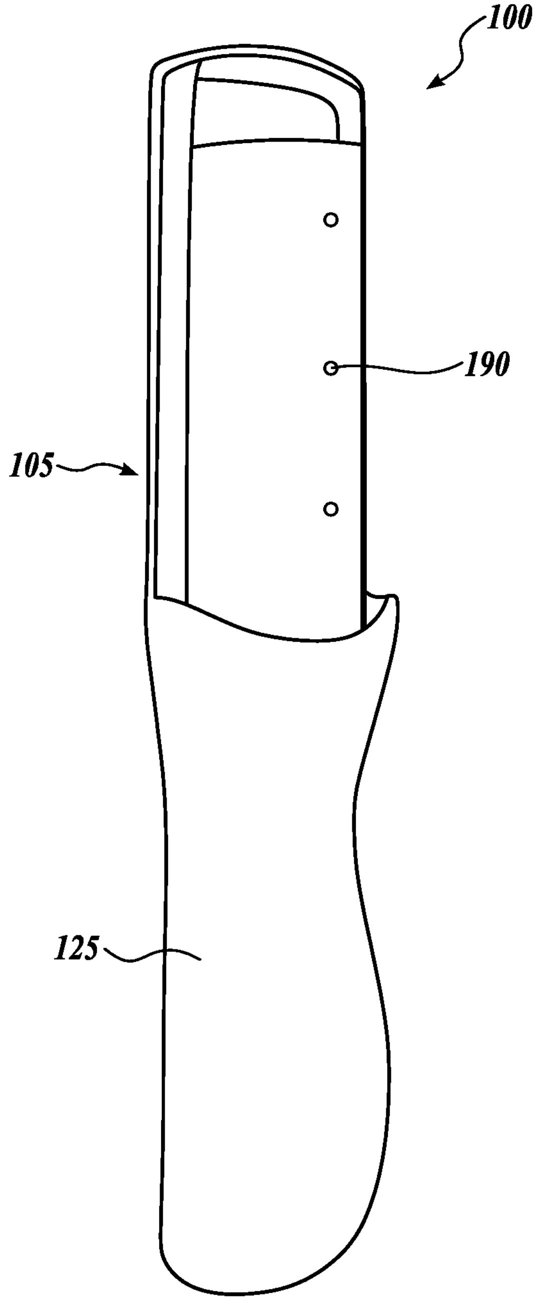

FIGS. 1A-1B are example skincare devices, in accordance with the present technology. The skincare device 100 may include a body 105, a cartridge 110, and an applicator 190. In some embodiments, the skincare device 100 also has a handle 125. In some embodiments, the handle 125 and the body 110 are removably attached, but in other embodiments, the handle 125 and the body 110 are a single piece. In some embodiments, the skincare device 100 includes a user input 135.

Figure 2:
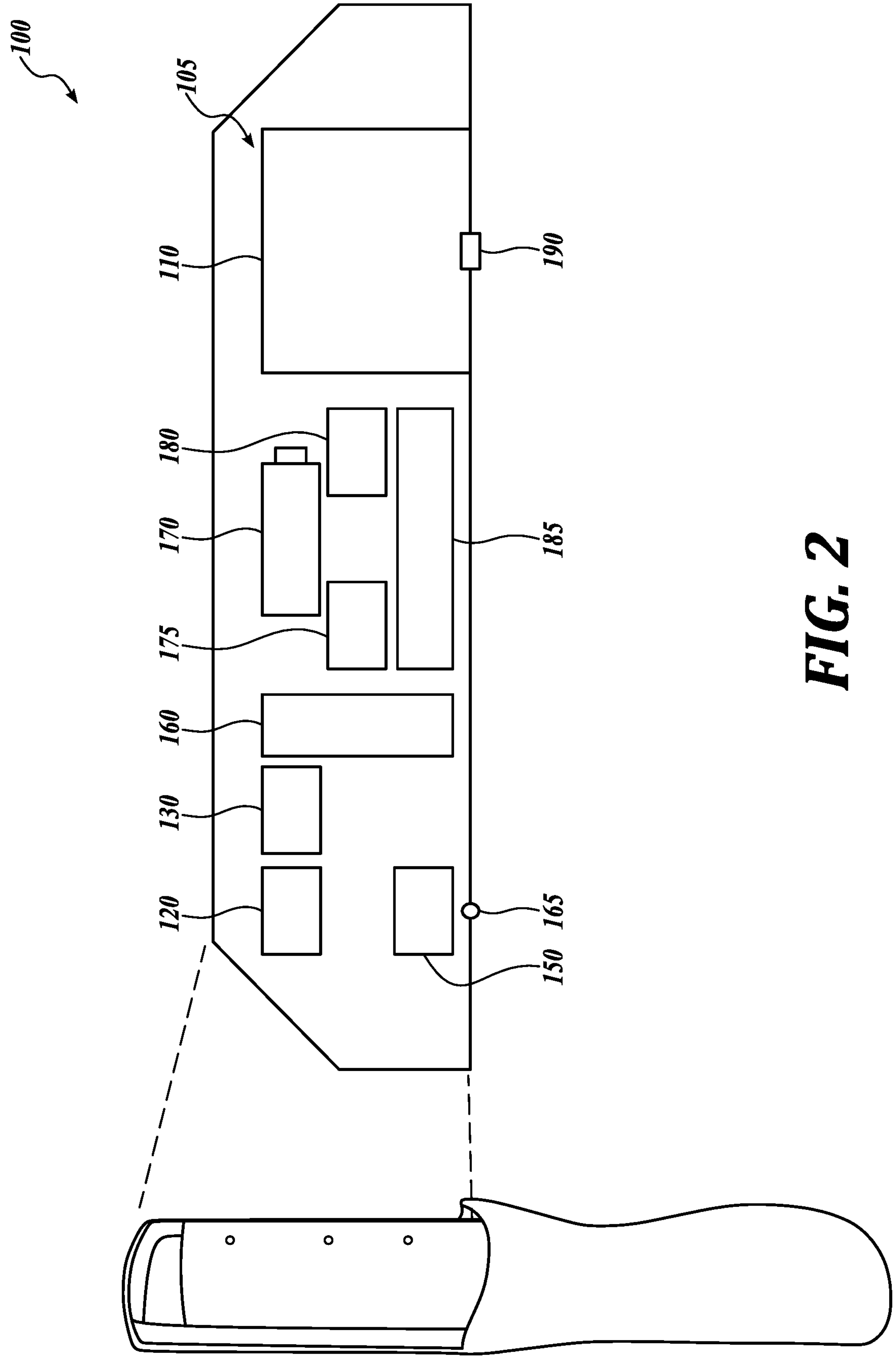
FIG. 2 is an internal view of an example skincare device, in accordance with the present technology.

As illustrated in FIG. 1A, the skincare device 100 may include a cartridge 110. In some embodiments, the skincare device 100 may have more than one cartridge 100. In some embodiments, the cartridge 110 may be attached to the body 105 of the skincare device 100, as illustrated in FIG. 1A, but in some embodiments, the cartridge may be disposed inside the body 105 of the skincare device 100 as illustrated in FIG. 2. In yet other embodiments, the cartridge 110 may be located on another portion of the skincare device 100, such as inside or on the handle 125.

In some embodiments, the cartridge 110 contains a skin formula. In some embodiments, the cartridge 110 includes a skin treatment, such as a wrinkle treatment or an acne treatment. In some embodiments, the skin formula is a cosmetic, such as a concealer, a brow tint, or an eyeliner. In some embodiments, the skin formula is a mixture of a wrinkle treatment or acne treatment and a concealer.

In some embodiments, the cartridge 110 has an identifier, such as a QR code or an RFID tag so that the skincare device 100 can identify the type of skincare formula.

While the user input 135 is illustrated as a button on FIG. 1A, the user input 135 can take any number of forms including a switch or a touch-type capacitive button. In operation, the user can actuate the user input to begin the imaging process described in detail herein. In some embodiments, the user can further actuate the user input to direct the device to apply the skincare formula.

In some embodiments, such as those illustrated by FIGS. 1A-1B, the applicator 190 is located on the body 105 of the skincare device 100. In some embodiments, the applicator is a mechanical pump. In some embodiments, the applicator is a solenoid pump. In some embodiments, the applicator is a microfluidic pump. In some embodiments, the applicator is a piezoelectric pump. In some embodiments, there is more than one applicator 190 on the skincare device 100. In some embodiments, all the applicators 190 dispense the same skin formula at different locations. In some embodiments, the applicators 190 may dispense different formulas, i.e. one applicator 190 dispenses wrinkle treatment, while another applicator 190 dispenses concealer. In some embodiments, the user can attach cartridge containing skin formula to the skincare device, apply the formula, and then swap out the cartridge for another cartridge containing a different skin formula, so the same applicator may dispense the first and the second skin formula. In operation, as a user moves the skincare device 100 over their face (as illustrated and described in FIG. 4), a skin formula may be dispensed by the applicator onto one or more features, providing a way to treat and/or conceal a portion of the user's skin.

FIG. 2 is an internal view of an example skincare device, in accordance with the present technology. In some embodiments, the skincare device 100 includes a cartridge 110, an accelerometer 120, a gyroscope 130, a contact sensor 150, a processor 160, a contact pin 165, a battery 170, an IR camera 175, a light source 180, and an optical system 185 disposed in the body 105 of the skincare device 100.

The illustrated skincare device 100 includes an accelerometer 120 and a gyroscope 130. In some embodiments, the accelerometer 120 and the gyroscope 130 are communicatively coupled to the processor 160. In operation, the accelerometer 120 measures the vibration or acceleration of the skincare device in the x, y, and z direction to determine the orientation of the skincare device 100. The gyroscope 130, in operation similarly detects the angular velocity and orientation of the skincare device 100.

In some embodiments, the skincare device 100 includes a contact sensor 150, communicatively coupled to the processor 160. In some embodiments, the contact sensor is configured to sense proximity to the user's skin. In some embodiments, the contact sensor is also communicatively coupled to a contact pin 165. In some embodiments, the contact pin is located on the same face of the skincare device 100 as the applicator 190. In operation, as a user moves the skincare device 100 across his or her face, the contact pin 165 detects the proximity between the skincare device 100 and the user's face (not pictured in FIG. 2). The contact pin can communicate this proximity to the contact sensor 150, which can likewise communicate to the processor 160, and then determine if the skincare device 100 is in close enough proximity to the face and a feature of the face to apply the skincare formula. While there is only a single contact pin 165 illustrated in FIG. 2, the skincare device 100 may have any number of contact pins 165. In some embodiments, each individual contact pin 165 gives a separate proximity so that skin formula is only applied by the applicator(s) 190 in the area in sufficient proximity with the user's face.

In some embodiments, the skincare device 100 includes a battery 170. Though battery 170 is further described, the skincare device 100 can include other power sources, for example, capacitors. In an embodiment, the battery 170 is a rechargeable battery 170 configured to receive electrical power from an external source when, for example, electrical power of the rechargeable battery 170 has been depleted. In another embodiment, the battery 170 is a single-use battery 170. In an embodiment, a useable life of the single-use the battery 170 corresponds to an intended use interval of the skincare device 100. As the skincare device 100 is used over time, it may become worn, dirty, or otherwise unsuitable to provide its intended benefits. In this regard, as the single-use battery 170 is used up and runs out of power, the skincare device 100 may be configured to signal to a user that the skincare device 100 is ready for replacement, cleaning, reconditioning, and the like.

In some embodiments, the skincare device 100 further includes an IR camera 175, a light source 180, and an optical system 185 communicatively coupled to the processor 160. In some embodiments, the light source 180 and the IR camera 175 are communicatively coupled to the optical system 185. In some embodiments, the skincare device further comprises an optical system configured to determine if the light conditions are suitable for detecting the one or more features of the user's skin. In some embodiments, the optical system 185 can sense as to whether the user is in adequate lighting conditions to detect a feature on the user's skin with the IR camera, as described in more detail in FIG. 3. If it is determined that the user is not in adequate lighting conditions, the light source 180 may illuminate the user's face to better detect the user's features. If this is still not enough light to detect the user's features, such as if the user is in a dark room, the skincare device 100 may alert the user to move to another location. After the lighting conditions are determined to be adequate to detect the user's features, the IR camera may visualize an image of the user's face.

As the user moves the skincare device 100 over his or her face, the IR camera visualizes images of the user's skin. The processor can then assign a probability to each pixel of each image as being either (1) a feature, (2) a facial landmark, or (3) normal skin based on the color of each pixel. In some embodiments, the feature is a wrinkle, a fine line, pigmentation, hyper pigmentation, or acne. In some embodiments, the feature is detected based on the color of the pixel. In some embodiments, the feature ranges from pink to red. In some embodiments, the feature is any color that is not the color of the user's normal skin. For example, the processor 160 may identify hyper pigmentation on a user's skin by identifying pixels that are pink or red in color. The processor can then apply a skin formula, such as a concealer to the area that is pink or red. In another example, the processor 160 may identify acne on a user's skin by detecting pixels that are pink or red in color and apply both an acne treatment and a concealer to the user's acne.

In some embodiments, the processor 160 detects wrinkles or fine lines on the user's face by detecting pixels that are darker in color than the user's skin tone on the user's face in an unbroken line segment across the user's face. In some embodiments, the processor assigns a probability to each pixel as being either a wrinkle or the user's unblemished skin based on color. In some embodiments, the processor 160 can then direct the applicator 190 to apply either a wrinkle treatment, a concealer, or both, effectively treating and concealing the wrinkle or fine line.

In some embodiments, the processor 160 sets a probability threshold for determining whether or not to apply skin formula to the pixels that have a probability of being a skin feature, such as a wrinkle, fine line, acne, pigmentation, or hyper pigmentation. In some embodiments, the probability threshold is hardcoded into the processor 160. In some embodiments, the probability threshold may be adjusted to the user's preferences or needs. For example, the threshold may need to higher if the skin feature and the user's skin tone are not very distinct from each other. The threshold may likewise be lowered when the desired skincare and the undesired skincare are distinct from one another, such as when a user has a lighter skin tone, and the feature is red or pink in color. In some embodiments, the probability threshold is set at 85%, 90%, 95%, or 100%. If a pixel exceeds the probability threshold, the processor 160 directs the applicator 190 to apply skin formula to that specific area. In some embodiments, the processor 160 can detect one or more wrinkles by detecting an unbroken line of pixels on the user's face. In this case, if the average of the pixels within the unbroken segment exceeds the probability threshold, the processor 160 can direct the applicator 190 to apply the skin formula to the entire wrinkle on the user's face. In some embodiments, the applicator is configured to move so that it can apply the skin formula to the wrinkle without requiring the user to move the applicator over the wrinkle.

In some embodiments, the processor can determine the facial features of the user through a facial landmark algorithm. In some embodiments, when the processor 160 identifies a facial feature, the processor directs the applicator 190 to apply the skin formula. In some embodiments, the facial feature is an upper lash line, a lower lash line, a waterline, or an eyebrow. For example, the processor 160 may identify a user's upper lash line with a facial landmark algorithm, and then apply eyeliner to the user's upper lash line. In another example, the processor may identify a user's eyebrow with a facial landmark algorithm, and then apply brow tint to the user's eyebrow.

Figure 3:
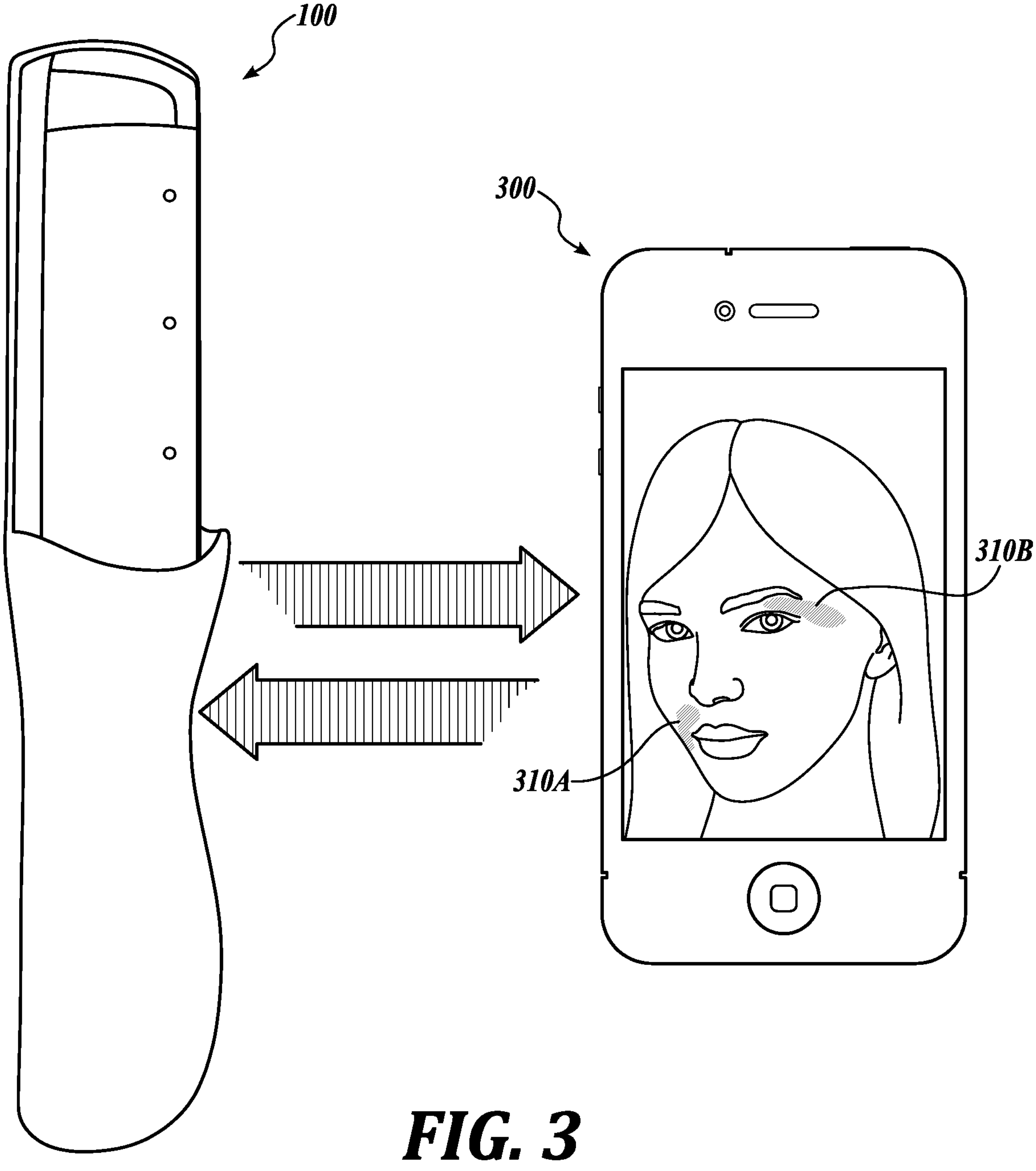
FIG. 3 is an example skincare system, in accordance with the present technology.

FIG. 3 is an example skincare system, in accordance with the present technology. In some embodiments, the skincare device 100 is communicatively coupled to a communication device 300. Although the communication device 300 is illustrated as a smartphone, the communication device 300 may take the form of a personal computer (PC), a laptop computer, a PDA (Personal Digital Assistants), a smart phone, a tablet device, a UMPC (Ultra Mobile Personal Computer), a net-book, or a notebook type personal computer.

The communication device 300 is capable of performing wireless communication with the skincare device 100 by way of a wireless communication interface circuitry on the skincare device 100. However, communication device 300 is also capable of having a wired connection to the skincare device 100 by way of a USB interface on the skincare device. Additionally, each device, including the skincare device 100, may communicate with each other and the external one or more devices through an internet connection via an 802.11 wireless connection to a wireless internet access point, or a physical connection to the internet access point, such as through an Ethernet interface. Each connected communication device 300 is capable of performing wireless communication with other devices, such as through a Bluetooth connection or other wireless means as well.

The connected communication device 300 is configured to receive information from a user for use to start the imaging process and/or start applying skin formula. In some embodiments, the communication device 300 includes a user interface that allows a user to visualize one or more features 310*a*, 310*b* on the users face that treatment will be applied to. In some embodiments, these features 310*a*, 310*b* are highlighted or colored on the user interface to allow the user to better visualize the features. The feature 310*a* is an example wrinkle on the user's face that has been highlighted on the user interface. The feature 310*b* is an example eyebrow on the user's face that has been highlighted on the user interface. In some embodiments, the user can select one or more of the features 310*a*, 310*b* that are highlighted on the user interface to apply the skin formula to.

Figure 4:
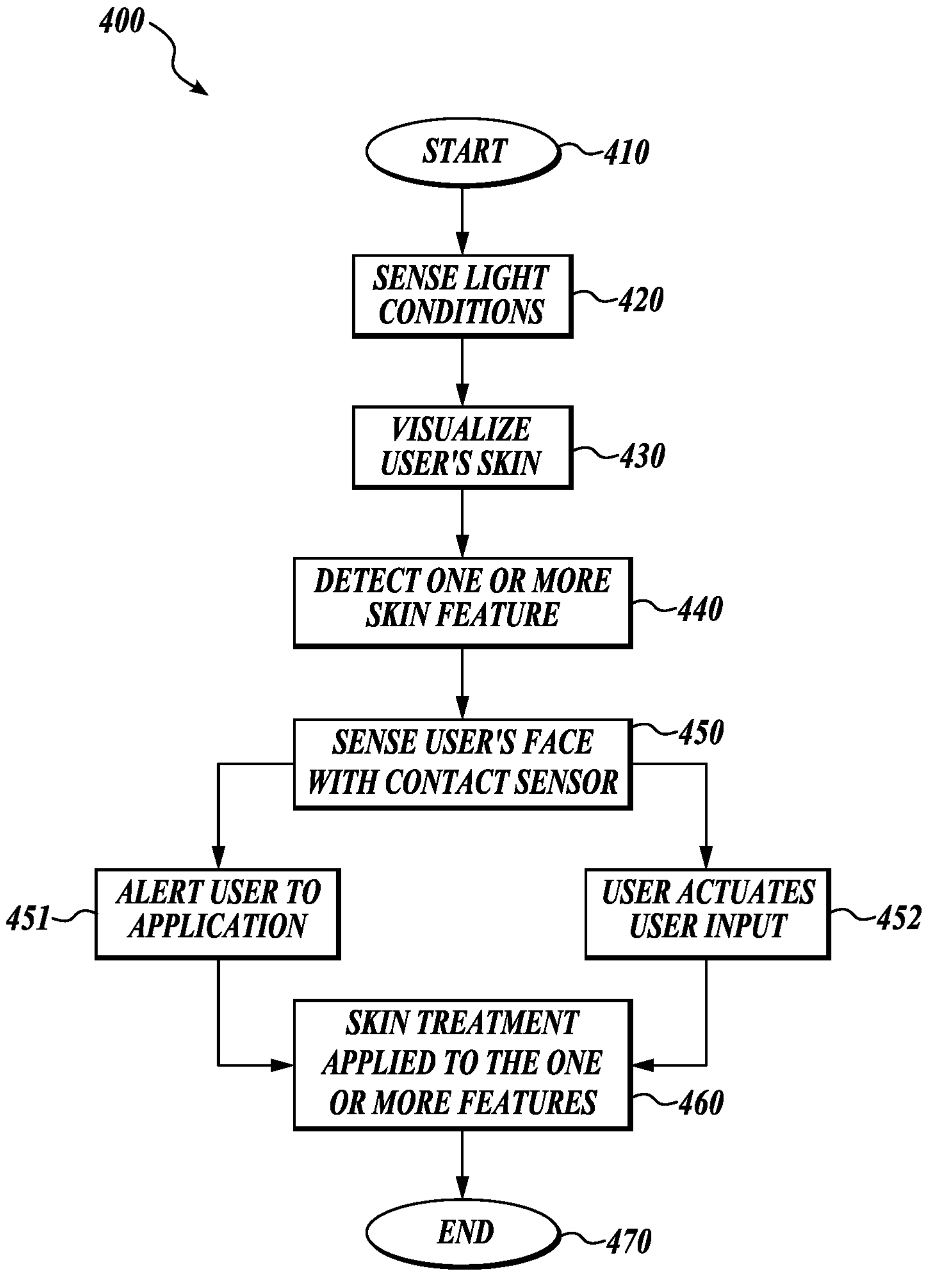
FIG. 4 is a flowchart of a method of treating a feature on a user's skin, in accordance with the present technology.

FIG. 4 is a flowchart of a method of treating a feature on a user's skin 400, in accordance with the present technology. In block 410, the method starts.

In block 420, the system optionally senses the light conditions in the location the user is at. The light conditions may be sensed with a light sensor. In some embodiments, the light sensor is on a dispensing device (such as dispensing device 100). In other embodiments, the light sensor is on a communication device (such as communication device 300). In some embodiments, the light sensor takes a light reading of the surrounding area to ensure that it will be able to visualize the user's skin and skin features as described herein. In some embodiments, the dispensing device, the communication device, or both alert the user to move into more optimal conditions to begin the visualization. In some embodiments, the user initiates the light sensor reading by actuating a user-input on the dispensing device or the communication device.

In block 420, the user's skin is visualized. In some embodiments, the user's skin is visualized with an image sensor or camera on the dispensing device, but in other embodiments, the user's skin is visualized with a communication device, such as the camera of a smartphone. In some embodiments, the user can move the dispensing device over their skin, such as their face. In some embodiments, the user may select a particular location, such as their eyebrows, cheeks, or forehead.

In block 430, the dispensing device detects one or more features on the user's skin with an image sensor. In some embodiments, the feature is a wrinkle, a fine line, pigmentation, hyper pigmentation, or acne. In some embodiments, the feature is an upper lash line, a lower lash line, a waterline, or an eyebrow. In operation the dispensing device, or the communication device, can detect the one or more features with image processing. In some embodiments, the dispensing device or communication device can detect the one or more features with cross-polarized light image processing. In some embodiments, the system can detect wrinkles by detecting discontinuing lines on the surface of a user's skin. In some embodiments, the system can detect wrinkles by detecting different types of curves on the surface of a user's skin. In some embodiments, a user's eyebrows can be detected by detecting large discontinuing lines on a user's face. In some embodiments, the system can detect landmarks, such as the eyes, eyebrows, nose, etc. In some embodiments, the one or more features can be detected by detecting color in a predetermined range, such as in the case of detecting pigmentation, hyperpigmentation, or acne. In some embodiments, the predetermined range of color is from pink to dark red. In some embodiments, the predetermined range of color is the color of the user's eyebrows. In this manner, the device can detect one or more features and conceal, color, or treat them with precision.

Optionally, in block 440, the dispensing device senses its proximity to the user's skin with a contact sensor. In some embodiments, the user can move the device closer to or farther from their skin in order to ensure the skincare material is applied correctly, as described herein, in the target areas of the one or more features. In some embodiments, the dispenser alerts the user to move the device closer or farther from their skin. In some embodiments, the communication device alerts the user to move the device closer or farther from the user's skin.

Optionally, in block 451, the dispensing device alerts the user that it will start applying the skin formula. In some embodiments, the alert is an auditory alert. In some embodiments, the alert is a tone or a blinking LED. In some embodiments, the alert is issued on the communication device instead of the dispensing device. Alternatively, in block 452, the dispensing device waits to apply the skin formula until it receives a command from the user.

In some embodiments, the command is given by the user by actuating a user input. In some embodiments, the user input is a button, touch pad, or switch. In some embodiments, the command is given with the communication device, such as by a user actuating the touch screen of the communication device in response to a notification or pop up on the communication device.

In block 460, the skin formula is applied to the user's skin in the detected locations. In some embodiments, the user can move the dispensing device over their skin to apply the skin formula. In some embodiments, block 460 happens simultaneously with blocks 430 and 440, so as the dispensing detects the one or more features and ensures it is in proximity with the user's skin, it also applies the skin formula to the user's skin.

In operation, a user can move the dispensing device over their skin, the device can detect, for example, any wrinkles on the user's face, and the device can immediately apply wrinkle treatment and concealer to the user's wrinkles. Optionally, the user can move the dispensing device over their face times to ensure any wrinkles they have are filled in, treated, and concealed.

In block 470, the method ends.

Figure 5:
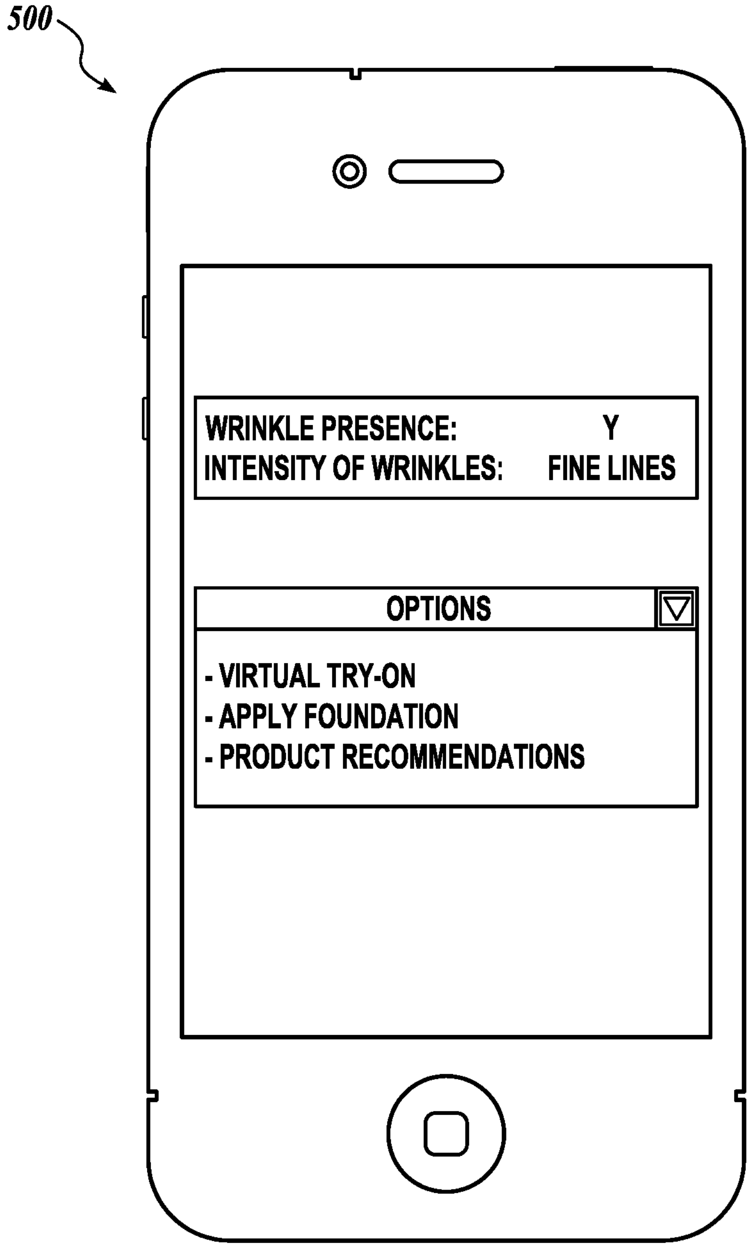
FIG. 5 is an example dashboard configured to be used in connection with skin care devices as described herein, in accordance with the present technology.

FIG. 5 is an example dashboard 500 configured to be used in connection with skin care devices 100 as described herein, in accordance with the present technology. In some embodiments, a skin care device 100 is configured to communicatively couple with a smart device, such as a smartphone as illustrated in FIG. 3. In some embodiments, the smart device may take the form of a personal computer, tablet, laptop, or the like.

In some embodiments, the smart device is configured to display a dashboard 500. In some embodiments, the dashboard 500 may be displayed on the skin care device 100 itself.

In some embodiments, the dashboard 500 includes outputs to a user. In some embodiments, the outputs include an indicator of whether wrinkles are present and an intensity of wrinkles. These outputs should be understood as merely representative, and any sort of outputs may be included.

In some embodiments, the intensity of the wrinkles is determined by how deep the wrinkles are. For example, a user who has deep wrinkles would be considered to have "high" intensity wrinkles, while a user with fine lines would be considered to have "low" intensity wrinkles. In some embodiments, the output categorizes the wrinkles, such as by indicating the intensity as "deep" or "fine line", such as shown in FIG. 5.

In some embodiments, the dashboard 500 further includes a set of options. While the options are illustrated as a drop-down menu, it should be understood that the options may be arranged and/or displayed in any form. In some embodiments, the options include a virtual try on, a button to apply a foundation or other skin care product, and product recommendations.

In some embodiments, the virtual try on will allow a user to see a desired foundation color or skin care product on themselves using the camera of the smart device. In some embodiments, the virtual try on allows a user to take a photo of their skin or face and overlay a desired color on the photo. In some embodiments, the virtual try on allows a user to use the camera of the smart device to capture images or video in real-time and overlay the color, finish, or treatment over the real time images or video of the user's skin.

In some embodiments, the apply foundation (or other skin care products) option acts as an actuator for the skin care device (such as skin care device 100). In such embodiments, the user can actuate the apply foundation option (such as by pressing a button or utilizing a touch screen) to apply the foundation from the skin care device. In some embodiments, actuating the "apply foundation" option results in dispensing a different skin care product, such as an acne treatment, a moisturizer, a primer, a bb or cc cream, or the like.

Embodiments disclosed herein may utilize circuitry in order to implement technologies and methodologies described herein, operatively connect two or more components, generate information, determine operation conditions, control an appliance, device, or method, and/or the like. Circuitry of any type can be used. In an embodiment, circuitry includes, among other things, one or more computing devices such as a processor (e.g., a microprocessor), a central processing unit (CPU), a digital signal processor (DSP), an application-specific integrated circuit (ASIC), a field-programmable gate array (FPGA), or the like, or any combinations thereof, and can include discrete digital or analog circuit elements or electronics, or combinations thereof.

In an embodiment, circuitry includes one or more ASICs having a plurality of predefined logic components. In an embodiment, circuitry includes one or more FPGA having a plurality of programmable logic components. In an embodiment, circuitry includes hardware circuit implementations (e.g., implementations in analog circuitry, implementations in digital circuitry, and the like, and combinations thereof). In an embodiment, circuitry includes combinations of circuits and computer program products having software or firmware instructions stored on one or more computer readable memories that work together to cause a device to perform one or more methodologies or technologies described herein. In an embodiment, circuitry includes circuits, such as, for example, microprocessors or portions of microprocessor, that require software, firmware, and the like for operation. In an embodiment, circuitry includes an implementation comprising one or more processors or portions thereof and accompanying software, firmware, hardware, and the like. In an embodiment, circuitry includes a baseband integrated circuit or applications processor integrated circuit or a similar integrated circuit in a server, a cellular network device, other network device, or other computing device. In an embodiment, circuitry includes one or more remotely located components. In an embodiment, remotely located components are operatively connected via wireless communication. In an embodiment, remotely located components are operatively connected via one or more receivers, transmitters, transceivers, or the like.

An embodiment includes one or more data stores that, for example, store instructions or data. Non-limiting examples of one or more data stores include volatile memory (e.g., Random Access memory (RAM), Dynamic Random Access memory (DRAM), or the like), non-volatile memory (e.g., Read-Only memory (ROM), Electrically Erasable Programmable Read-Only memory (EEPROM), Compact Disc Read-Only memory (CD-ROM), or the like), persistent memory, or the like. Further non-limiting examples of one or more data stores include Erasable Programmable Read-Only memory (EPROM), flash memory, or the like. The one or more data stores can be connected to, for example, one or more computing devices by one or more instructions, data, or power buses.

In an embodiment, circuitry includes one or more computer-readable media drives, interface sockets, Universal Serial Bus (USB) ports, memory card slots, or the like, and one or more input/output components such as, for example, a graphical user interface, a display, a keyboard, a keypad, a trackball, a joystick, a touch-screen, a mouse, a switch, a dial, or the like, and any other peripheral device. In an embodiment, circuitry includes one or more user input/output components that are operatively connected to at least one computing device to control (electrical, electromechanical, software-implemented, firmware-implemented, or other control, or combinations thereof) one or more aspects of the embodiment.

In an embodiment, circuitry includes a computer-readable media drive or memory slot configured to accept signal-bearing medium (e.g., computer-readable memory media, computer-readable recording media, or the like). In an embodiment, a program for causing a system to execute any of the disclosed methods can be stored on, for example, a computer-readable recording medium (CRMM), a signal-bearing medium, or the like. Non-limiting examples of signal-bearing media include a recordable type medium such as any form of flash memory, magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, a wired communications link, a wireless communication link (e.g., transmitter, receiver, transceiver, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

The detailed description set forth above in connection with the appended drawings, where like numerals reference like elements, are intended as a description of various embodiments of the present disclosure and are not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result. Generally, the embodiments disclosed herein are non-limiting, and the inventors contemplate that other embodiments within the scope of this disclosure may include structures and functionalities from more than one specific embodiment shown in the figures and described in the specification.

In the foregoing description, specific details are set forth to provide a thorough understanding of exemplary embodiments of the present disclosure. It will be apparent to one skilled in the art, however, that the embodiments disclosed herein may be practiced without embodying all the specific details. In some instances, well-known process steps have not been described in detail in order not to unnecessarily obscure various aspects of the present disclosure. Further, it will be appreciated that embodiments of the present disclosure may employ any combination of features described herein.

The present application may include references to directions, such as "vertical," "horizontal," "front," "rear," "left," "right," "top," and "bottom," etc. These references, and other similar references in the present application, are intended to assist in helping describe and understand the particular embodiment (such as when the embodiment is positioned for use) and are not intended to limit the present disclosure to these directions or locations.

The present application may also reference quantities and numbers. Unless specifically stated, such quantities and numbers are not to be considered restrictive, but exemplary of the possible quantities or numbers associated with the present application. Also in this regard, the present application may use the term "plurality" to reference a quantity or number. In this regard, the term "plurality" is meant to be any number that is more than one, for example, two, three, four, five, etc. The term "about," "approximately," etc., means plus or minus 5% of the stated value. The term "based upon" means "based at least partially upon."

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

The embodiments of the invention in which an exclusive property or privilege is claimed are defined as follows:

1. A system for treating skin, the system comprising:

at least one cartridge containing a skin formula;

a dispensing device configured to accept the at least one cartridge and comprising an applicator, the dispensing device including a light sensor configured to determine if light conditions are suitable for detecting the one or more facial features on skin with an infrared camera, wherein determining if light conditions are suitable comprises taking a light reading of a surrounding area, the infrared camera, one or more contact pins located on a same face of the dispensing device as the applicator, and a removably attached handle; and a processor communicatively coupled to the dispensing device, wherein the processor is configured to:

visualize an image of a user's skin with the infrared camera;

when the light conditions are not suitable, alert the user to move the user to another location;

detect one or more features on the user's skin with image processing, wherein the image processing comprises assigning a probability to each pixel of the image as being either a feature, a facial landmark, or normal skin based on a color of each pixel;

set a probability threshold for determining whether or not to apply the skin formula to a designated area based on the image processing;

detect a proximity between the dispensing device and a user's face with a contact pin;

determine if the dispensing device meets a proximity threshold to the face and a feature of the face to apply the skincare formula; and when the designated area exceeds the probability threshold and the dispensing device meets the proximity threshold, apply the skin formula onto the one or more designated areas of the user's skin through the applicator on the dispensing device.

2. The system of claim 1, wherein the applicator is a piezoelectric pump.

3. The system of claim 1, wherein the applicator is a mechanical pump.

4. The system of claim 1, wherein the skin formula is a skin treatment.

5. The system of claim 1, wherein the skin treatment is an anti-wrinkle treatment.

6. The system of claim 1, wherein the skin treatment is an acne treatment.

7. The system of claim 1, wherein the skin formula is a cosmetic.

8. The system of claim 7, wherein the cosmetic is a concealer, an eyeliner, a brow tint, or a brow gel.

9. The system of claim 1, wherein the skin formula is both a skin treatment and a cosmetic.

10. The system of claim 1, wherein the feature is a wrinkle, a fine line, pigmentation, hyper pigmentation, or acne.

11. The system of claim 1, wherein the feature is an upper lash line, a lower lash line, a waterline, or an eyebrow.

12. A method of applying a skin treatment with the system of claim 1, the method comprising:

visualizing an image of a user's skin;

determining whether the light conditions are suitable for detecting the one or more features;

when the light conditions are not suitable, alerting the user to move to another location;

detecting one or more features on the user's skin with image processing, wherein the image processing comprises assigning a probability to each pixel of the image as being either a feature, a facial landmark, or normal skin based on a color of each pixel;

setting a probability threshold for determining whether or not to apply the skin formula to a designated area based on the image processing;

detecting a proximity between the dispensing device and a face with the contact pin;

determining if the dispensing device meets the proximity threshold to the face and a feature of the face to apply the skincare formula; and when the designated area exceeds the probability threshold and the dispensing device meets the proximity threshold, applying the skin formula onto the one or more features in the designated area of the user's skin through the applicator on the dispensing device.

13. The method of claim 12, wherein the system further comprises a communication device configured to visualize the user's skin on a user interface.

14. The method of claim 12, wherein the method further comprises issuing an alert to the user that the skin formula will be applied.

15. The method of claim 12, wherein the method further comprises actuating a user input to apply the skin formula.

16. The method of claim 12, wherein the feature is a wrinkle, a fine line, pigmentation, hyper pigmentation, or acne.

17. The method of claim 12, wherein the feature is an upper lash line, a lower lash line, a waterline, or an eyebrow.

* * * * *